(12) United States Patent
Beden et al.

(10) Patent No.: US 8,875,748 B2
(45) Date of Patent: Nov. 4, 2014

(54) DEVICE FOR FILLING A FILTER, AND METHOD THEREFOR

(75) Inventors: Josef Beden, Mainz-Kastel (DE); Itka Bado, Bad Homburg (DE); Georg Verch, Wiesbaden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 739 days.

(21) Appl. No.: 13/061,782

(22) PCT Filed: Sep. 2, 2009

(86) PCT No.: PCT/EP2009/006372
§ 371 (c)(1),
(2), (4) Date: Mar. 2, 2011

(87) PCT Pub. No.: WO2010/025912
PCT Pub. Date: Mar. 11, 2010

(65) Prior Publication Data
US 2011/0168291 A1    Jul. 14, 2011

(30) Foreign Application Priority Data
Sep. 2, 2008    (DE) .......................... 10 2008 045 422

(51) Int. Cl.
*A61M 1/16* (2006.01)
*B01D 61/30* (2006.01)
*A61M 1/36* (2006.01)
*B01D 65/00* (2006.01)

(52) U.S. Cl.
CPC .......... *A61M 1/3643* (2013.01); *A61M 1/1658* (2013.01); *B01D 61/30* (2013.01); *A61M 1/1607* (2013.01); *A61M 2205/3393* (2013.01); *B01D 65/00* (2013.01); *B01D 2313/16* (2013.01); *A61M 1/365* (2013.01)
USPC ................. 141/1; 141/94; 210/646; 210/239; 210/85; 210/321.72; 604/6.09

(58) Field of Classification Search
None
See application file for complete search history.

(56) References Cited

U.S. PATENT DOCUMENTS

| 5,733,257 | A |  | 3/1998 | Sternby |  |
|---|---|---|---|---|---|
| 5,770,064 | A | * | 6/1998 | Jonsson et al. | ................. 210/232 |
| 6,123,847 | A |  | 9/2000 | Bene |  |
| 6,277,272 | B1 |  | 8/2001 | Nikaido et al. |  |
| 6,331,252 | B1 |  | 12/2001 | El Sayyid et al. |  |
| 7,186,342 | B2 |  | 3/2007 | Pirazzoli et al. |  |
| 2007/0185430 | A1 |  | 8/2007 | Brugger et al. |  |

FOREIGN PATENT DOCUMENTS

| DE | 34 18 434 C2 | 6/1986 |
|---|---|---|
| DE | 42 40 681 A1 | 6/1994 |
| DE | 100 11 208 C1 | 9/2001 |
| DE | 698 21 415 T2 | 3/2005 |
| DE | 699 28 887 T2 | 7/2006 |

(Continued)

*Primary Examiner* — Terry Cecil
(74) *Attorney, Agent, or Firm* — Jacobson Holman, PLLC

(57) ABSTRACT

An apparatus for the filling of a medical filter has at least one first space and one second space which are semipermeably separated by one or more membranes, with the spaces each having at least one inflow and outflow. The apparatus includes a detection unit having a first element and a second element, with a liquid discharge from at least one of the first and second spaces being detectable by the first element, and the state of the filling of the filter being determinable by the second element with reference to the detected liquid discharge. A method of filling a medical filter employs the apparatus.

17 Claims, 4 Drawing Sheets

(56) References Cited

FOREIGN PATENT DOCUMENTS

| | | |
|---|---|---|
| DE | 601 26 817 T2 | 12/2007 |
| EP | 0 161 686 A2 | 11/1985 |
| EP | 0 723 463 A1 | 7/1996 |
| EP | 0 747 074 A1 | 12/1996 |
| EP | 1 100 559 | 5/2001 |
| EP | 1 395 311 | 3/2004 |
| EP | 1 457 218 A1 | 9/2004 |
| EP | 1 707 226 A1 | 10/2006 |
| JP | S62-120853 | 6/1987 |
| JP | 03-254755 | 11/1991 |
| JP | 08-332221 | 12/1996 |
| JP | 09-028791 | 2/1997 |
| JP | 2002-521141 | 7/2002 |
| WO | WO 95/10310 A1 | 4/1995 |
| WO | WO 00/06217 A1 | 2/2000 |
| WO | WO 02/32476 A2 | 4/2002 |
| WO | WO 02/098491 A1 | 12/2002 |

* cited by examiner

DEVICE FOR FILLING A FILTER, AND METHOD THEREFOR

CROSS-REFERENCE TO RELATED APPLICATIONS

This is a national stage of PCT/EP09/006372 filed Sep. 2, 2009 and published in German, which claims the priority of German number 10 2008 045 422.2 filed Sep. 2, 2008, hereby incorporated by reference.

BACKGROUND OF THE INVENTION

1. Field of Invention

The present invention relates to an apparatus for the filling of a medical filter and to a method therefor.

2. Description of the Prior Art

Such medical filters can be dialyzers, for example. Dialyzers can have a bundle of hollow fiber membranes which are enclosed in a housing and form a blood side and a dialysate side which are separated from one another by the plurality of hollow fiber membranes. Very generally, but in particular in dialysis, the problem must be faced before the putting into operation of a medical filter, in particular of a dialyzer, of completely deaerating or filling this filter. The filter is therefore prepurged with a liquid and thereby deaerated for the deaeration of the filter. With dialyzers, this is as a rule carried out during the setting up process of the dialysis machine using an isotonic saline solution (NaCl solution), with the NaCl solution being able to be admixed with an anticoagulant such as heparin.

In the preparation or filling of the filter and also of the extracorporeal blood circuit, the filter is often filled together with the hose system, for example in "continuous venovenous hemodialysis (CVVHD)" or "continuous venovenous hemodiafiltration (CVVHDF)", such that the inflowing liquid initially runs in from below on the blood side with a dialyzer arranged perpendicular. The air is thus ideally upwardly displaced and e.g. conveyed into a waste bag via the upper venous connection of the dialyzer.

Since, in the counterflow process, the dialysate flows through the dialysate side with an opposite direction of flow in comparison with the blood side, the inflow and outflow at the dialysate side are arranged opposite to the inflow and outflow of the blood side of the dialyzer. On the filling of the filter, the problem thus arises that, with a filling of the dialysate side via the membrane from a blood side, in particular with a dialyzer arranged perpendicular, the outflow of the dialysate side is located at the lower end adjacent to the inflow of the dialyzer at the blood side so that on a filling via the membrane only a partial filling is adopted at the dialysate side. A complete deaerating is only ensured if the filter is rotated after the filling of the blood side and before the filling of the dialysate side.

This problem is solved in already known systems in that it is indicated to the operator to rotate the filter accordingly after the filling of the blood side. A further known solution approach consists of filling the blood circuit with a reverse connection by flow reversal on the blood side and hereby to make a rotation unnecessary. Such an approach is, however, complex and/or expensive since additional pumps and sensor devices are required.

It has furthermore been found that a filling of a filter with a rotary procedure enables a particularly reliable deaeration or filling of the filter. The procedure is established and recognized in clinics. It would therefore be desirable also to continue first to fill the blood side from the bottom to the top in order hereby reliably to displace the air from the blood side and then to rotate the dialyzer in order subsequently to deaerate and fill the dialysate side. This procedure of filling via the membrane from the blood side into the dialysate side furthermore has the advantage of also deaerating the pores of the membranes. In the normal case, the blood inlet in this process is at the upper end of the dialyzer during the later treatment. This arrangement is advantageous simply because the blood thereby does not have to be conveyed against gravity, which is accompanied by less stress for the blood. If, however, in this procedure, the rotation of the filter is forgotten after the prompt or if the dialyzer is already incorrectly connected from the start, the filling of the dialysate side can generally not take place completely and the effectiveness of the treatment drops due to reduction of the effective filter surface. Furthermore, in particular with systems which carry out a dialysate/filtrate balance by means of scales, alarm messages/triggering of alarms can occur due to residual air entry into the balancing containers. Further disadvantages consist of the fact that coagulation can be stimulated by remaining residual air in the filter in the later treatment which could result in partial clogging of the membranes.

SUMMARY OF THE INVENTION

It is therefore the object of the present invention to further develop an apparatus and a method of the initially named kind in an advantageous manner, in particular such that a medical filter can be filled safely and reliably and/or an incorrect filling of a medical filter can be reliably recognized.

This object is satisfied in accordance with the invention by an apparatus for the filling of a medical filter having the features described herein. Provision is accordingly made that an apparatus for the filling of a medical filter has at least one filter having at least a first space and a second space which are semipermeably separated by one or more membranes, with the spaces each having at least one inflow and outflow and with the apparatus having a detection unit having first and second means, with liquid discharge from at least one of the spaces being detectable by means of the first means and the state of the filling of the filter being able to be determined with reference to the detected liquid discharge by means of the second means. Such an apparatus for the filling of a medical filter can in this respect have conveying means for the filling of the filter with liquid, for example a circulation pump which is arranged in front of the first space of the filter and a removal or filtrate pump after the outflow of the second space. It is possible to draw a conclusion on the state of filling of the filter by the detection of the liquid discharge from at least one of the spaces. For instance, on a filling process in which the first space is filled in a first step, for example, a liquid discharge from the first space means that the first space is completely filled. Applied to the filling process described above of a dialyzer arranged perpendicular for the filling process, this means that the filter would now have to be rotated to deaerate the filter at the dialysate side.

It is of advantage if the inflows and outflows of the first and second spaces are arranged such that the at least one filter is operated in counterflow, with the first space first being filled by means of the apparatus for filling and with the filter being rotated by approximately 180° after the filling of the first space and the second space being filled by liquid overflow from the first space via the membrane or membranes. The membranes can in this respect be hollow fiber membranes of a dialyzer. This procedure allows the clinically recognized procedure for the filling or deaerating of a dialyzer to be monitored at the apparatus side by means of the detection unit. A monitored, complete filling of the filter hereby becomes possible.

Provision can be made that a filling volume for the filling of the filter is preset and/or stored in the apparatus and that a correct filling of the filter is determined by means of the second means of the detection unit if a liquid discharge from the second space is detected by means of the first means after dispensing of the filling volume to the filter. This filling volume can be oriented on the filling volume of the dialyzer and is advantageously dimensioned to be slightly larger than the filling volume of a filter or of the dialyzer. The dead volume of the hose set to be used is advantageously likewise to be included in the filling volume. It thereby becomes possible for example by comparison of a stored value with the conveyed volume detected by means of a conveying device, to recognize at the apparatus side when the complete filling volume for the filling of the filter has been dispensed to the filter. In particular in the case in which first the first space is filled from the bottom to the top, then the filter is rotated by 180° and subsequently the second space is filled from the first space via the membrane, the outflow of the second space is located at the upper end of the dialyzer so that a liquid discharge can only take place when both the first and the second spaces of the filter, and thus the total filter, are completely filled.

It is furthermore conceivable that a filling volume for the filling of the filter is preset and/or stored in the apparatus and that an incorrect filling of the filter is determined by means of the second means of the detection unit if a liquid discharge from the second space is detected by means of the first means during the dispensing of the filling volume to the filter. It is conceivable in this connection that, with a perpendicular arrangement with an inflow of a first space arranged at the bottom, on a filling of the first space, the first space is first filled from the bottom to the top. If the filter is subsequently not rotated or is not completely rotated, liquid is dispensed outwardly on a filling of the dialysate side via the membrane through the incorrectly disposed, i.e. then still downwardly disposed, outflow of the second space so that a conclusion can be drawn from this liquid discharge from the second space on an incorrect arrangement of the filter and thus on an incorrect filling of the filter. A detection of the incorrect filling at the machine side or at the apparatus side is thereby made possible.

It is conceivable that the first means include at least one sensor which detects the liquid discharge from at least one of the spaces with reference to weight and/or volume and/or flow rate and/or conductivity. A sensor can thus be made such that it detects the weight of the fluid discharged, for example, from the second space. It is, however, equally possible, additionally or as a single measurement method, to determine the volume of the outflowing fluid. Furthermore, flow rate sensors and/or conductivity sensors are already now provided in dialysis machines, for example, by means of which a liquid outflow can likewise be detected. All the aforesaid sensors are now already used in corresponding dialysis machines so that already present transducers can advantageously be used for the detection of the filling state.

Provision can be made that a collection apparatus is provided after the second space for the reception of liquid flowing out of the second space and that the first means include a weighing device or are made as a weighing device which determines the weight of the collection apparatus. Such a weighing device is in particular present in CVVHD or CVVHDF machines having a filling device of a dialyzer so that it is possible to make use of already present components for the apparatus in accordance with the invention. It is thus conceivable in this connection that, after the filling of the blood side, the dialysate side is filled via the membrane by rotation of the filter and passage through the, for example, correspondingly arranged blood and filtrate pump. The air is now conveyed from the filter into the filtrate bag. Provided that the filter was correctly rotated, a certain time passes due to the conveying in of the necessary volume until the air has been completely displaced from the filter and liquid is discharged at the upper outlet of the second space. This liquid then moves into the waste bag and thus to the scales. A weight increase at the scales is only detected after conveying of this volume which essentially corresponds to the filling volume of the dialyzer on the dialysate side. It thus becomes possible to use this delayed weight signal at the scales for the recognition of the filter rotation which has taken place and of the complete filling of the filter. In the case in which the filter had not been correctly rotated or had been incorrectly connected right from the start, the dialysate flows directly to the lower dialysate connection without any substantial delay after the filling of the first space, that is, directly to the outflow of the second space, so that the time delay up to the weight increase in the filtrate bag is absent, whereby it is recognized at the apparatus side that an incorrect and incomplete filling of the filter is present.

Provision can be made that the second means are made such that a threshold for the liquid discharge is stored in the second means and a liquid discharge which is detected by the first means, lies below a preset threshold value and occurs during the filling of the filter is discounted and is not taken into account for the evaluation of the filling state. It thereby becomes possible to be able to take account of tolerances in the filling volume, in particular of the disposable hose set and to set the sensitivity of the detection unit, but also to be able to readjust it.

It is furthermore conceivable that a partial filling volume is preset for the filling of the filter, with the partial filling volume being slightly larger than the filling volume of the first space, and that the state of the outflow from the second space can be determined by means of the second means of the detection unit, with an open outflow being recognized by the second means if, after dispensing of the partial filling volume, a liquid discharge from the second space is determined by the first means and/or a closed outflow of the second space is recognized if, after dispensing of the partial filling volume, no liquid discharge from the second space is determined by the first means. It thereby becomes possible to make use of the circumstance according to which, on the correct filling of the blood side, i.e. on the complete filling of the first space or on the prefilling of the dialyzer inflow, filling takes place slightly above the filling volume of the first space and the slight liquid amount which overflows from the first into the second space and flows directly over the downwardly disposed outflow of the second space into the filtrate bag is used for a detection whether any possible closure is present in the feed line to the waste bag, for example a forgotten clamp. If a clamp, and thus a closure, should be present, no weight increase can be detected in the waste bag. It is conceivable in this connection to remove the liquid volume additionally used for this purpose or to include it in the filling balancing, for example by an adaptation of the threshold value. It is in particular of advantage in this connection that a recognition of a closure of the waste line is possible at a relatively early time so that any possible additional complications resulting from this can be avoided in advance.

It is preferred if the apparatus is part of a medical device, in particular of a dialysis machine. It is particularly advantageous if it is a CVVHD or a CVVHDF machine.

The invention furthermore relates to a method for the filling of a medical filter having the features described herein. Provision is accordingly made that, on the filling of a medical filter, with the filter having at least a first space and a second space which are semipermeably separated by one or more membranes and with the spaces each having an inflow and an outflow and being filled sequentially, the liquid discharge from at least one of the spaces is detected and the state of the filling of the filter is determined with reference to the detected liquid outflow.

Provision can furthermore be made that the inflows and outflows of the first and second spaces are arranged such that the at least one filter is operated in counterflow, with the first space first being filled by means of the apparatus for filling and with the filter being rotated by approximately 180° after the filling of the first space and the second space being filled by liquid overflow from the first space via the membrane or membranes.

It is furthermore conceivable that a correct filling of the filter is determined if a liquid discharge from the second space is detected by means of the first means after dispensing of a preset filling volume to the filter and/or an incorrect filling of the filter is determined if a liquid outflow from the second space is detected by means of the first means during the dispensing of a preset filling volume to the filter. The filling volume can be oriented on the filling volume of the filter as well as on the dead volume of the hose set and can, for example, be stored in a dialysis machine or in an apparatus for the filling of a medical filter. It is equally or additionally possible to proportion the liquid volume required for the filling of the filter by means of a filling bag with filling liquid provided especially for this purpose and to connect this filling bag to the hose set for the filling.

It is moreover conceivable that the liquid discharge from at least one of the spaces is detected with reference to the weight and/or volume and/or flow rate and/or conductivity of the liquid flowing out of the filter.

It is furthermore possible that a collection apparatus is provided after the second space for the reception of liquid flowing out of the second space and that the weight of the collection apparatus is detected and evaluated for the determination of the liquid discharge.

It is of advantage if a threshold value for the liquid discharge is preset and that a liquid discharge present below a preset threshold value and occurring during the filling of the filter is discounted and is not taken into account for the evaluation of the filling state. It is conceivable in this connection to set a threshold value as a percentage value of the filling volume, that is, of the volume which is necessary for the filling of the filter and of the associated hose set.

The state of the outflow from the second space can be determined in that a partial filling volume is preset for the filling of the filter, with the partial filling volume being slightly larger than the filling volume of the first space and with an open outflow of the second space being recognized after filling the first space and before a rotation of the filter in that, after dispensing of the partial filling volume, a liquid discharge from the second space is determined and/or a closed outflow from the second space is recognized in that no liquid discharge from the second space is determined after dispensing of the partial filling volume.

BRIEF DESCRIPTION OF THE DRAWINGS

Further details and advantages of the invention will now be explained in more detail with reference to an embodiment shown in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
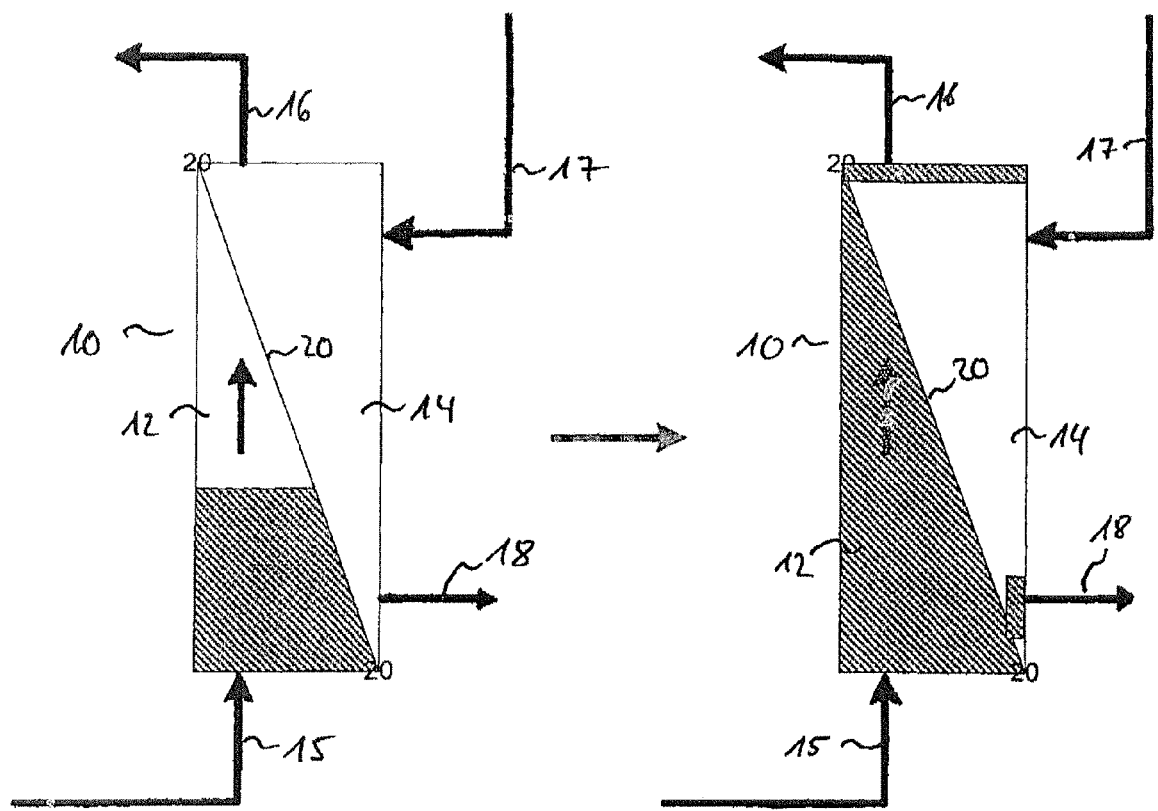
FIG. 1: a schematic representation of the filling process of the blood side of a dialysis machine.

FIG. 1 schematically shows the filling of a medical filter 10, here a dialysis machine 10, wherein the arterial inflow 15, that is, the inflow of the blood side 12, is arranged at the lower end of the dialyzer 10 arranged perpendicular.

The apparatus in accordance with the invention is part of a dialysis machine which uses medical filters 10 preferably made as dialyzers 10 with a plurality of hollow fiber membranes 20, with the hollow membranes 20 combined in the manner of a bundle in a dialyzer housing separating the blood side 12 semipermeably from the dialysate side 14. The blood side 12 and the dialysate side 14 of the dialyzer 10 each have separate inflows and outflows 15, 16, 17, 18. The blood side 12 in this respect has a downwardly disposed arterial inlet 15 for the filling process and an upwardly disposed venous backflow 16, whereas the dialysate side has an upwardly disposed dialysate inflow 17 and a downwardly disposed filtrate outflow 18. It is preferred if the detection unit 30 of the apparatus for the filling of a medical filter 10 is formed by already present components of the dialysis machine. It is conceivable in this connection that the first means which detect the liquid discharge, for example from the dialysate side 14 or from the blood side 12 of the dialyzer 10, are formed by sensors of the dialysis machine. The second means by means of which the state of the filling of the filter 10 is determined can in particular advantageously be formed by the machine control of the dialysis machine or also by a separate control module which is in communication with the machine control of the dialysis machine.

As shown in FIG. 1, the inflows and outflows of the first and second spaces, that is, of the dialysate side 14 and of the blood side 12 of the dialyzer 10, are arranged such that the dialyzer 10 is operated in counterflow. For the filling of the filter 10, the blood side 12 is filled first, as is shown in FIG. 1. In this respect, a primer solution, for example comprising a sodium chloride solution which is advantageously admixed with heparin, is filled from the bottom to the top by means of pumps not shown in any more detail, for example by means of the circulation pump of the blood side or the blood pump of the extracorporeal circuit of the dialysis machine.

This filling process of the blood side 12 of the filter 10 is carried out for so long until, as shown at the right in FIG. 1, the blood side 12 is completely filled. A rotation of the dialyzer 10 by 180° then takes place.

Figure 2:
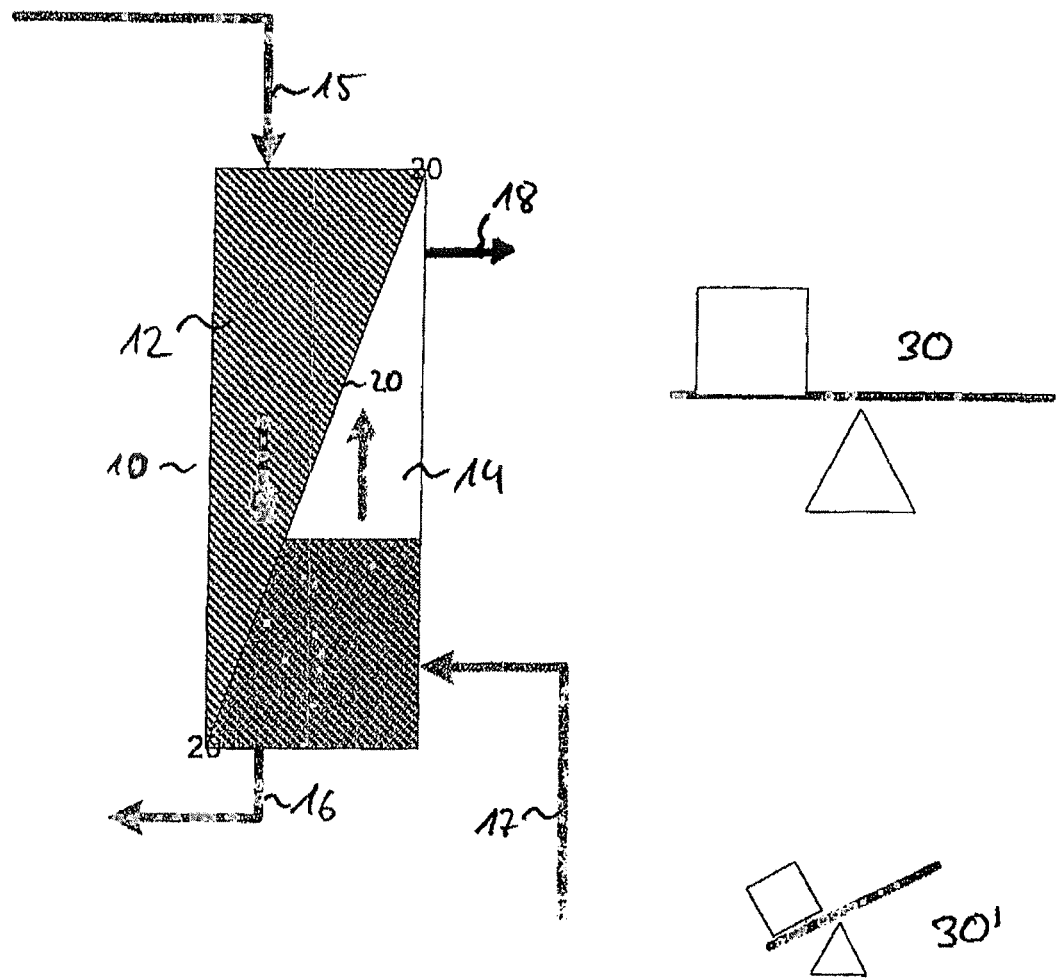
FIG. 2: a schematic representation of the filling procedure of the dialysate side of a dialyzer on a correct rotation.

After the rotation by 180° counterclockwise, as is shown in FIG. 2, a filling of the dialysate side 14 takes place via the membranes of the dialyzer 10. Provision can be made in this respect that the venous backflow 16 and the dialysate inflow 17 for the filling of the dialysate side 14 are disconnected or that liquid is removed by means of a filtrate pump, not shown, at the filtrate outflow 18. Sine the filtrate outflow 18 of the dialysate side 14 is located at the upper end of the dialyzer 10, a liquid discharge from the filtrate outflow can only occur when the dialysate side 14 is completely filled. Only then can the weight signal be detected by means of a weighing device 30, which is shown schematically, said weight signal being generated by the liquid discharge from the filtrate outflow 18. The detected weight signal is put into relation with the stored filling volume of the dialyzer 10 by the machine control so that a complete filling of the dialyzer 10 is recognized. This weight signal is detected by the scales 30', as is shown in the lower right hand part of FIG. 2. The filling volume is calculated in this respect from the volume required for the complete filling of the dialyzer 10 plus the dead volume for the hose systems.

Figure 3:
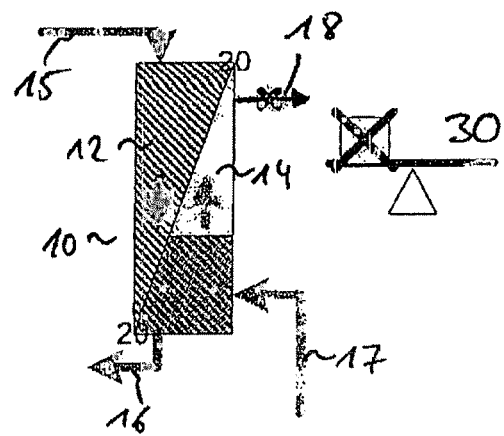
FIG. 3: a schematic representation of the filling of the dialysate side of a dialyzer on an incorrect outflow or an incomplete filling.

FIG. 3 schematically shows the case wherein no scales signal is detected by means of the scales 30 after the dispensing of the maximum filling volume on the part of the filling apparatus. This indicates that errors have occurred in the routine, as the case may be leaks in the hose system, and an incomplete filling of the dialyzer 10 has occurred.

Figure 4:
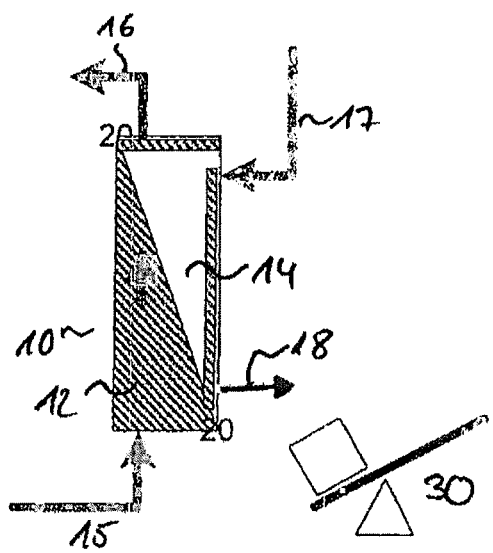
FIG. 4: a schematic representation of the filling process of a dialyzer without a filter rotation.

FIG. 4 shows the case wherein the dialyzer 10 has not been rotated by 180° after the complete filling of the blood side 12. A further filling via the membrane to the dialysate side 14 results directly in a liquid discharge from the filtrate outflow 18 which is located in the lower part of the dialyzer 10 in the arrangement shown in FIG. 4. A liquid discharge occurs which is directly detected by means of the scales 30. Seen in relation with the filling volume, it is detected at the machine side that a scales signal has occurred during the filling procedure, which is equated with a missing filter rotation at the machine side. It is conceivable in this connection to output this operating error by means of a warning signal, for example optically and acoustically at the dialysis machine.

Figure 5:
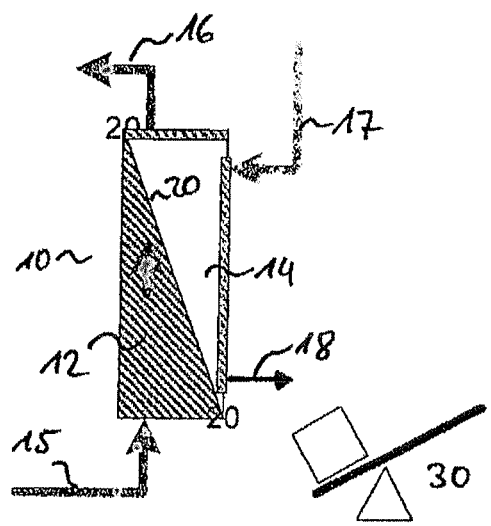
FIG. 5: a schematic representation of the recognition of an open connection or outflow on the dialysate side.

FIG. 5 shows a special embodiment of the apparatus in accordance with the invention and of the method in accordance with the invention. In this connection, a partial filling volume for the filling of the filter 10 is preset which is slightly larger than the filling volume of the blood side 12 or the volume for the prefilling of the dialyzer input side 17 is slightly above the minimum amount required. This partial filling volume is completely conveyed into the dialyzer 10 so that a partial overflow over the membrane 20 into the dialysate side 14 or a partial filling of the dialysate side 14 occurs. This partial liquid overflow can be detected by means of the scales 30. At the machine side, it is then recognized with reference to the scales signal in conjunction with the information that the partial filling volume has been completely dispensed, that the filtrate outflow 18 is open.

Figure 6:
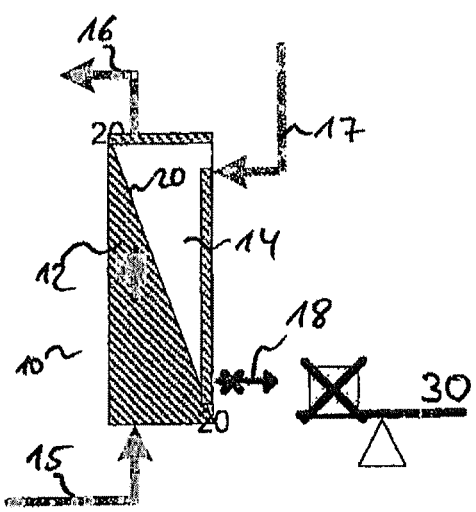
FIG. 6: a schematic representation of the recognition of a closed outflow on the dialysate side.

FIG. 6 accordingly shows the case wherein, likewise as in FIG. 5, the partial filling volume has been conveyed into the blood side 12 of the dialyzer 10, but the filtrate outflow 18 of the dialysate side 14 is blocked. It is not possible in this case to obtain a scales signal by means of the weighing device 30. At the machine side, it is recognized from this signal combination comprising a lack of a scales signal in conjunction with partial filling volumes completely conveyed into the blood side 10 that the filtrate outflow 18 of the dialysate side 14 of the dialyzer 10 is blocked. This defective state can then likewise be output at the machine side as an optical and/or acoustic warning signal, for example via the monitor of the dialysis machine.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for filling a medical filter, comprising:
    at least one filter having at least one first space and one second space which are semipermeably separated by one or more membranes, with the at least one first space and one second space each having at least one inflow and outflow; and
    a detection unit having a first element and a second element, with a liquid discharge from at least one of the first and second spaces being detectable by the first element, and a state of the filling of the filter being determinable by the second element with reference to the detected liquid discharge,
    the filter being configured to be rotated by approximately 180° after the filling of the first space and before the filling of the second space, and
    the apparatus being configured to determine, based on the detected liquid discharge, whether the filter has been properly rotated during the filling thereof.

2. The apparatus for filling a medical filter in accordance with claim 1, wherein inflows and outflows of the at least one first and second spaces are arranged such that the at least one filter is operated in counterflow, with the first space being filled by the apparatus, and with the second space being filled by liquid overflow from the first space via the one or more membranes.

3. The apparatus for filling a medical filter in accordance with claim 1, wherein a filling volume for the filling of the filter is at least one of preset and stored in the apparatus, and wherein a correct filling of the filter is determined by the second element of the detection unit if a liquid discharge from the second space is detected by the first element of the detection unit after dispensing of the filling volume to the filter.

4. The apparatus for filling a medical filter in accordance with claim 1, wherein a filling volume for the filling of the filter is at least one of preset and stored in the apparatus, and wherein an incorrect filling of the filter is determined by the second element of the detection unit if a liquid discharge from the second space is detected by the first element of the detection unit after dispensing of the filling volume to the filter.

5. The apparatus for filling a medical filter in accordance with claim 1, wherein the first element of the detection unit includes at least one sensor which detects the liquid discharge from at least one of the first and second spaces with reference to at least one of a weight, a volume, a flow rate, and a conductivity.

6. The apparatus for filling a medical filter in accordance with claim 1, further comprising a collection apparatus for the reception of liquid flowing out of the second space provided after the second space, and wherein the first element of the detection unit includes a weighing device or is configured as a weighing device which determines a weight of the collection apparatus.

7. The apparatus for filling a medical filter in accordance with claim 1, wherein the second element of the detection unit stores a threshold value for the liquid discharge, and a liquid discharge which is detected by the first element of the detection unit, is below a preset threshold value and occurs during the filling of the filter is discounted and is not taken into account for the determination of the filling state.

8. The apparatus for filling a medical filter in accordance with claim 1, wherein a partial filling volume is preset for the filling of the filter, with the partial filling volume being slightly larger than the filling volume of the first space, and wherein the state of an outflow from the second space can be determined by the second element of the detection unit, with an open outflow being recognized by the second element if, after dispensing of the partial filling volume, at least one of a liquid discharge from the second space is determined by the first element and a closed outflow of the second space is recognized if, after dispensing of the partial filling volume, no liquid discharge from the second space is determined by the first element.

9. The apparatus for filling a medical filter in accordance with claim 1, wherein the apparatus is part of a medical device.

10. The apparatus for filling a medical filter in accordance with claim 9, wherein the medical device is a dialysis machine.

11. A method of filling a medical filter having at least one first space and one second space which are semipermeably separated by one or more membranes, with the at least one first space and one second space each having at least one inflow and outflow, and a detection unit having a first element and a second element, with a liquid discharge from at least one of the first and second spaces being detectable by the first element, and a state of the filling of the filter being determinable by the second element with reference to the detected liquid discharge, the filter being configured to be rotated by approximately 180° after the filling of the first space and before the filling of the second space, and the apparatus being configured to determine, based on the detected liquid discharge, whether the filter has been properly rotated during the filling thereof, said method comprising:
    filling the first space of the filter;
    rotating the filter by approximately 180° after the filling of the first space;
    detecting the liquid discharge from at least one of the first and second spaces; and
    determining the state of the filling of the filter with reference to the detected liquid discharge.

12. The method of filling a medical filter in accordance with claim 11, wherein inflows and outflows of the first and second spaces are arranged such that the at least one filter is operated in counterflow, with the first space being filled first, and the second space being filled by liquid overflow from the first space via the one or more membranes.

13. The method of filling a medical filter in accordance with claim 11, wherein at least one of a correct filling of the filter is determined if a liquid discharge from the second space is detected by the first element of the detection unit after dispensing of a preset filling volume to the filter, and an incorrect filling of the filter is determined if a liquid discharge from the second space is detected by the first element of the detection unit during the dispensing of a preset filling volume to the filter.

14. The method of filling a medical filter in accordance with claim 11, wherein the liquid discharge from at least one of the first and second spaces is detected with reference to at least one of a weight, a volume, a flow rate, and a conductivity of the liquid discharged from the filter.

15. The method of filling a medical filter in accordance with claim 11, wherein a collection device for receiving liquid flowing out of the second space is provided after the second space, and further comprising a step of detecting and evaluating a weight of the collection apparatus for determining the liquid discharge.

16. The method of filling a medical filter in accordance with claim 11, wherein a threshold value for the liquid discharge is preset, and wherein a liquid discharge which is below the preset threshold value and which occurs during the filling of the filter is suppressed and is not taken into account for the determining of the filling state.

17. The method of filling a medical filter in accordance with claim 11, wherein the state of an outflow from the second space is determined in that a partial filling volume for the filling of the volume is preset, with the partial filling volume being slightly larger than the filling volume of the first space and with an open outflow of the second space being recognized after the filling of the first space and before rotating the filter in that at least one of a liquid discharge from the second space is determined after dispensing the partial filling volume, and a closed outflow of the second space is detected in that no liquid discharge from the second space is determined after dispensing of the partial filling volume.

\* \* \* \* \*